United States Patent [19]

Kincey

[11] Patent Number: 5,066,805
[45] Date of Patent: Nov. 19, 1991

[54] CATALYTIC HYDROGENATION OF 2-AMINO-6-CHLOROPURINE

[75] Inventor: Peter M. Kincey, Epsom, England

[73] Assignee: Beecham Group, p.l.c., Brentford, England

[21] Appl. No.: 381,584

[22] Filed: Jul. 18, 1989

[30] Foreign Application Priority Data

Jul. 20, 1988 [GB] United Kingdom ................ 8817270

[51] Int. Cl.⁵ .......................................... C07D 473/32
[52] U.S. Cl. ..................................... 544/277; 544/276
[58] Field of Search ......................................... 544/277

[56] References Cited

U.S. PATENT DOCUMENTS

| | | | |
|---|---|---|---|
| 4,609,662 | 9/1986 | Krenitsky | 514/262 |
| 4,649,140 | 3/1987 | Schaeffer | 514/261 |
| 4,736,029 | 4/1988 | Harnden et al. | 544/277 |
| 4,965,270 | 10/1990 | Harnden et al. | 514/262 |

FOREIGN PATENT DOCUMENTS 0182024  5/1986  European Pat. Off. ............ 544/277

OTHER PUBLICATIONS

Bendich, et al., J. Am. Chem. Soc., vol. 76, pp. 6073-6077 (1954).

Kusmierek, et al., Acta Chem. Scand., ser. B 1987, B41(10), pp. 701-707 (1987).

*Primary Examiner*—Diana Rivers
*Attorney, Agent, or Firm*—Hopgood, Calimafde, Kalil, Blaustein & Judlowe

[57] ABSTRACT

A process for the preparation of a compound of formula (I):

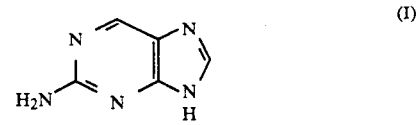

which process comprises the reduction of a compound of formula (II):

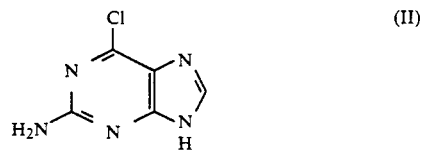

by catalytic hydrogenation using palladium on charcoal as catalyst.

4 Claims, No Drawings

CATALYTIC HYDROGENATION OF 2-AMINO-6-CHLOROPURINE

The present invention relates to a process for the preparation of a compound which is useful as an intermediate in the preparation of compounds which are antiviral agents.

The compound 2-aminopurine of formula (I):

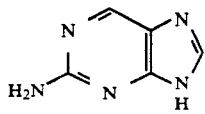

(I)

is a potentially useful intermediate in the preparation of 6-deoxy guanine nucleoside analogues, for example as described in EP-A-108285 (The Wellcome Foundation Limited), EP-A-182024 (Beecham Group p.l.c.) and EP-A-186640 (Astra Läkemedal Aktiebolag).

A suitable method of preparation involves the condensation of a side chain intermediate RQ wherein R is a side chain residue or a moiety convertible thereto, and Q is a leaving group, with the compound of formula (I), wherein the amino group is optionally protected, followed by subsequent conversion of R and deprotection, if necessary to give a compound of formula (A):

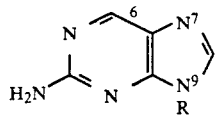

(A)

Compounds of formula (A) which are antiviral agents include the following:

| Compound | R |
| --- | --- |
| 6-Deoxyacyclovir | —(CH$_2$)$_4$OH |
| 6-Deoxy DHPG | —OCH$_2$CH(CH$_2$OH)$_2$ |
| 6-Deoxy DHBG | —(CH$_2$)$_2$CH(OH)CH$_2$OH |
| BRL 42810 | —(CH$_2$)$_2$CH(CH$_2$OAc)$_2$ |

Present preferred methods for obtaining compounds of formula (A) involve condensation of RQ with alternative compounds to 2-aminopurine, such as guanine itself or 2-amino-6-chloropurine, followed by an additional conversion step of 6—OH/6—Cl to 6-hydrogen. This is because 2-aminopurine itself is relatively expensive and not easily obtainable commercially, and a reliable, or high yielding method synthesis has not been available.

Kusmierek et al. (Acta Chem. Scand., Ser. B41: 701–707) have described a method of preparation of 2-aminopurine from 2-amino-6-chloropurine by electrolytic reduction.

We have now discovered an improved method which has the advantages of simplicity and hence is less expensive, and has greater potential for large scale production.

Accordingly, the present invention provides a process for the preparation of a compound of formula (I):

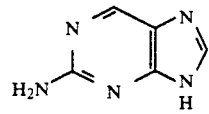

(I)

which process comprises the reduction of a compound of formula (II):

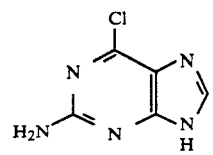

(II)

by catalytic hydrogenation using palladium on charcoal as catalyst.

The reaction usually takes place in an aqueous solution preferably in the presence of a base, such as sodium hydroxide, at a temperature of 5° C. to 100° C., preferably around 50° C.

The hydrogenation takes place at a pressure of 15 psi to 1500 psi (10.5 to 1050° kPa), preferably 100 psi (5200 mm Hg or 700 kPa), for a period of 75 min. to 24 hours, preferably about 3 hours.

The product is extracted by conventional methods, such as those described in the Example hereinafter.

The following Example illustrates the invention. The following Preparation Example describes the use of the compound of formula (I) in the preparation of BRL 42810.

EXAMPLE

2-Aminopurine

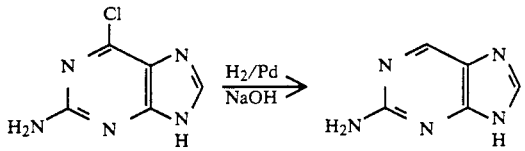

2-Amino-6-chloropurine (84.8 g, 0.5 mol) was dissolved in a solution of sodium hydroxide (50.0 g, 1.25 mol) in water (500ml). The resulting solution was added to 5% palladium on charcoal (10.0 g) and hydrogenated at 100 psi and 50° C. for 3 hours. The catalyst was filtered off, the filtrate was acidified to pH 8.0 with 2M hydrochloric acid, and the solution filtered to remove solid impurities. The filtrate was then further acidified to pH 5.5 and allowed to stand at 4° C. overnight. The precipitated product was filtered off, washed with ice-cold water, then acetone, and dried in vacuo at 50° C.

Yield 56.6, (83%) m.p. 277° C.

$^1$H nmr (d$_6$-DMSO) δ6.35(br s,2H,NH$_2$), 8.13(s,1H,H8), 8.65(s,1H,H6).

PREPARATION EXAMPLE

BRL 42810 from 2-aminopurine

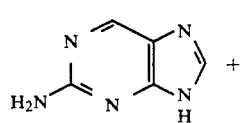 +

-continued

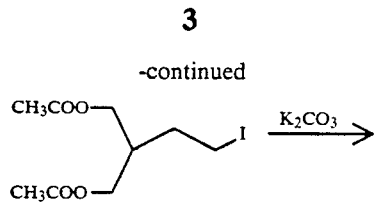

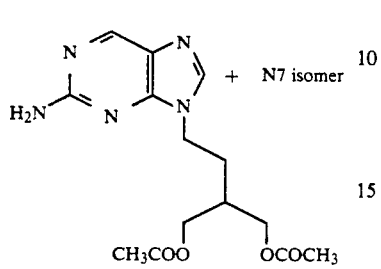

A mixture of 2-aminopurine (3.4 g, 0.025 mol), 2-acetoxymethyl-4-iodo-butyl-1-acetate (7.9 g, 0.025 mol), anhydrous potassium carbonate (5.2 g, m0.0375 mol) and dry dimethylformamide (50 ml) was stirred under nitrogen at room temperature for 18 hours. The mixture was filtered through celite, and the filter bed washed with dimethylformamide (50ml), the combined filtrates were evaporated to an oil, which was purified by column chromatography on silica gel (150 g), eluting with 95% chloroform/5% methanol, to give BRL 42810 as a white solid.

Yield 4.7 g (58%) m.p. 102° C.

$^1$H nmr (d$_6$-DMSO) δ1.88(m,3H), 2.00(s,6H), 4.03(d,4H), 4.14(t,2H), 6.45(br s,2H), 8.09(s,1H), 8.57(s,1H).

I claim:

1. A process for the preparation of a compound of formula (I):

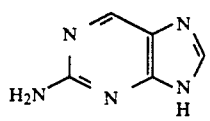

which process comprises the reduction in an aqueous solution in the presence of a base essentially devoid of an organic solvent of a compound of formula (II):

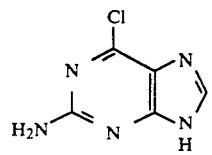

by catalytic hydrogenation using palladium on charcoal as catalyst.

2. A process according to claim 1 wherein the base is sodium hydroxide.

3. A process according to either of claims 1 or 2 wherein the reaction is carried out at a temperature of around 50° C.

4. A process according to either of claims 1 or 3 wherein the hydrogenation takes place at a pressure of around 70° kPa.

* * * * *

UNITED STATES PATENT AND TRADEMARK OFFICE
CERTIFICATE OF CORRECTION

PATENT NO.  : 5,066,805
DATED       : November 19, 1991
INVENTOR(S) : Peter M. Kincey It is certified that error appears in the above-indentified patent and that said Letters Patent is hereby corrected as shown below:

Column 4

Claim 4, line 3, change "70° kPa" to —700 kPa—.

Column 2 line 25, change "1050° kPa" to —10500 kPa—.

Signed and Sealed this

Twenty-sixth Day of October, 1993

Attest:

BRUCE LEHMAN

*Attesting Officer*    *Commissioner of Patents and Trademarks*